(12) United States Patent
Royer et al.

(10) Patent No.: US 11,277,487 B2
(45) Date of Patent: Mar. 15, 2022

(54) PROXY SERVER INTERFACE FOR BIODFEEDBACK DEVICE

(71) Applicant: DRROYER, PLLC, Grandville, MI (US)

(72) Inventors: Timothy G. Royer, Grandville, MI (US); Aaron Kenneth Blackwell, Paris, VA (US)

( * ) Notice: Subject to any disclaimer, the term of this patent is extended or adjusted under 35 U.S.C. 154(b) by 0 days.

(21) Appl. No.: 17/123,220

(22) Filed: Dec. 16, 2020

(65) Prior Publication Data

US 2021/0185141 A1 Jun. 17, 2021

Related U.S. Application Data

(60) Provisional application No. 62/948,543, filed on Dec. 16, 2019.

(51) Int. Cl.
*A61B 5/00* (2006.01)
*H04L 67/561* (2022.01)
*H04L 67/02* (2022.01)
*H04L 67/55* (2022.01)

(52) U.S. Cl.
CPC .......... *H04L 67/2804* (2013.01); *A61B 5/002* (2013.01); *A61B 5/486* (2013.01); *A61B 5/72* (2013.01); *H04L 67/02* (2013.01); *H04L 67/26* (2013.01)

(58) Field of Classification Search
CPC ....... A61B 5/00; A61B 5/0002; A61B 5/0004; H04L 67/26; H04L 67/2804; H04L 67/02
See application file for complete search history.

(56) References Cited

U.S. PATENT DOCUMENTS

| | | | | |
|---|---|---|---|---|
| 7,593,767 B1 * | 9/2009 | Modarres | ............. | A61B 5/4818 600/544 |
| 2008/0287817 A1 * | 11/2008 | Stivoric | ................ | A61B 5/318 600/508 |
| 2014/0228701 A1 * | 8/2014 | Chizeck | ............. | G06F 21/6254 600/544 |
| 2015/0157256 A1 * | 6/2015 | Galeev | ................... | A61B 5/721 600/301 |
| 2017/0310409 A1 * | 10/2017 | Yamagishi | ........... | H04N 21/454 |
| 2018/0279919 A1 * | 10/2018 | Bansbach | ................ | A61B 5/45 |

* cited by examiner

*Primary Examiner* — Chirag R Patel
(74) *Attorney, Agent, or Firm* — Benjamin C. Rothermel, Esq.

(57) ABSTRACT

A method for utilizing a proxy server interface includes measuring at least one of physiological or neurological functions of a subject by a hardware sensor in a measurement system, the hardware sensor configured to generate a signal containing information of the at least one of physiological or neurological functions, manipulating the signal by a processor, the measurement system including a first memory configured to store the manipulated signal, outputting the signal to the proxy server interface, the proxy server interface configured to buffer the signal in a second memory, and polling the proxy server interface for the buffered signal by an Internet browser. Outputting the signal to the proxy server interface and polling the proxy server interface for the buffered signal occurs asynchronously.

11 Claims, 4 Drawing Sheets

Fig. 3

| Time (t + millisec) | Subject Biometrics from Measurement System(s) | | | | | | Cached Values in Proxy | | | | | |
|---|---|---|---|---|---|---|---|---|---|---|---|---|
| | BPM (f=1sec) | Heart (f=4sec) | Temp (f=500ms) | Beta (uV) | Alpha (uV) | BPM (f=1sec) | Heart (f=4sec) | Temp (f=500ms) | EEG: Beta | EEG: Alpha | EEG: Beta | EEG: Alpha |
| 0 | 9 | 62 | 98.2 | 82 | 50 | 9 | 62 | 98.2 | 82 | 50 | 82 | 50 |
| 100 | | | | 76 | 74 | 9 | 62 | 98.2 | 76 | 74 | | |
| 200 | | | | 84 | 89 | 9 | 62 | 98.2 | 84 | 89 | | |
| 300 | | | | 77 | 108 | 9 | 62 | 98.2 | 77 | 108 | | |
| 400 | | | | 85 | 115 | 9 | 62 | 98.2 | 85 | 115 | 85 | 115 |
| 500 | | | 98.2 | 73 | 107 | 9 | 62 | 98.2 | 73 | 107 | | |
| 600 | | | | 78 | 150 | 9 | 62 | 98.2 | 78 | 150 | | |
| 700 | | | | 75 | 96 | 9 | 62 | 98.2 | 75 | 96 | | |
| 800 | | | | 70 | 50 | 9 | 62 | 98.2 | 70 | 50 | 70 | 50 |
| 900 | | | | 80 | 79 | 9 | 62 | 98.2 | 80 | 79 | | |
| 1000 | 10 | | 98.6 | 72 | 125 | 10 | 62 | 98.6 | 72 | 125 | | |
| 1100 | | | | 86 | 52 | 10 | 62 | 98.6 | 86 | 52 | | |
| 1200 | | | | 82 | 95 | 10 | 62 | 98.6 | 82 | 95 | 82 | 95 |
| 1300 | | | | 76 | 139 | 10 | 62 | 98.6 | 76 | 139 | | |
| 1400 | | | | 89 | 76 | 10 | 62 | 98.6 | 89 | 76 | | |
| 1500 | | | 98.4 | 79 | 64 | 10 | 62 | 98.4 | 79 | 64 | | |
| 1600 | | | | 81 | 144 | 10 | 62 | 98.4 | 81 | 144 | 81 | 144 |
| 1700 | | | | 73 | 141 | 10 | 62 | 98.4 | 73 | 141 | | |
| 1800 | | | | 82 | 95 | 10 | 62 | 98.4 | 82 | 95 | | |
| 1900 | | | | 74 | 92 | 10 | 62 | 98.4 | 74 | 92 | | |
| 2000 | 9 | | 98.1 | 73 | 101 | 9 | 62 | 98.1 | 73 | 101 | 73 | 101 |
| 2100 | | | | 72 | 101 | 9 | 62 | 98.1 | 72 | 101 | | |
| 2200 | | | | 70 | 79 | 9 | 62 | 98.1 | 70 | 79 | | |
| 2300 | | | | 74 | 57 | 9 | 62 | 98.1 | 74 | 57 | | |
| 2400 | | | | 90 | 85 | 9 | 62 | 98.1 | 90 | 85 | 90 | 85 |
| 2500 | | | 98.3 | 73 | 136 | 9 | 62 | 98.3 | 73 | 136 | | |
| 2600 | | | | 78 | 124 | 9 | 62 | 98.3 | 78 | 124 | | |
| 2700 | | | | 70 | 129 | 9 | 62 | 98.3 | 70 | 129 | | |
| 2800 | | | | 71 | 91 | 9 | 62 | 98.3 | 71 | 91 | 71 | 91 |
| 2900 | | | | 73 | 118 | 9 | 62 | 98.3 | 73 | 118 | | |
| 3000 | 12 | | 98.4 | 90 | 96 | 12 | 62 | 98.4 | 90 | 96 | | |

PROXY SERVER INTERFACE FOR BIOFEEDBACK DEVICE

CROSS-REFERENCE TO RELATED APPLICATION

This application claims the benefit of U.S. Provisional Patent Application No. 62/948,543, filed on Dec. 16, 2019, which is hereby incorporated by reference for all purposes as if fully set forth herein.

BACKGROUND

Field

Exemplary embodiments relate to a proxy server interface.

Discussion of the Background

Biofeedback works by measuring physiological and neurological functions of a subject such as human, and providing operant conditioning or rewards by interfacing these measured functions with a computer or other electronic device. For example, a subject's heartrate may be measured and input into a computer that includes a graphical output. If the subject's heartrate is within a target range, then the graphical output is maintained. However, if the subject's heartrate is above or below the target range, then the graphical output is disrupted. Thus, the subject is rewarded by maintaining the target heartrate. Other measured physiological or neurological functions for biofeedback include brain waves or breathing patterns, measured to help address sleep and attention problems.

The above information disclosed in this Background section is only for enhancement of understanding of the background of the inventive concept, and, therefore, it may contain information that does not form the prior art that is already known in this country to a person of ordinary skill in the art.

SUMMARY

Exemplary embodiments provide a proxy server interface for a biofeedback device.

Additional aspects will be set forth in the detailed description which follows, and, in part, will be apparent from the disclosure, or may be learned by practice of the inventive concept.

According to exemplary embodiments, a method for utilizing a proxy server interface includes measuring at least one of physiological and neurological functions of a subject by a hardware sensor in a measurement system, generating a signal by the hardware sensor, the signal including measured information of the at least one of physiological and neurological functions, manipulating the signal by a processor, the measurement system including a first memory configured to store the manipulated signal, outputting the signal by the measurement system to the proxy server interface, buffering the signal by the proxy server interface in a second memory, polling the buffered signal by an Internet browser. Outputting the signal to the proxy server interface and polling the proxy server interface for the buffered signal occurs asynchronously.

According to exemplary embodiments, a method for utilizing a proxy server interface includes measuring at least one of physiological and neurological functions of a subject by a hardware sensor in a measurement system, the hardware sensor configured to generate a signal containing information of the at least one of physiological and neurological functions, manipulating the signal by a processor, the measurement system including a first memory configured to store the manipulated signal, outputting the signal to the proxy server interface, the proxy server interface configured to buffer the signal in a second memory, and polling the proxy server interface for the buffered signal by an Internet browser. Outputting the signal to the proxy server interface and polling the proxy server interface for the buffered signal occurs asynchronously.

The foregoing general description and the following detailed description are exemplary and explanatory and are intended to provide further explanation of the claimed subject matter.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

FIG. 3 is a table displaying data from a proxy server interface according to an exemplary embodiment.

DETAILED DESCRIPTION OF THE ILLUSTRATED EMBODIMENTS

Figure 1:
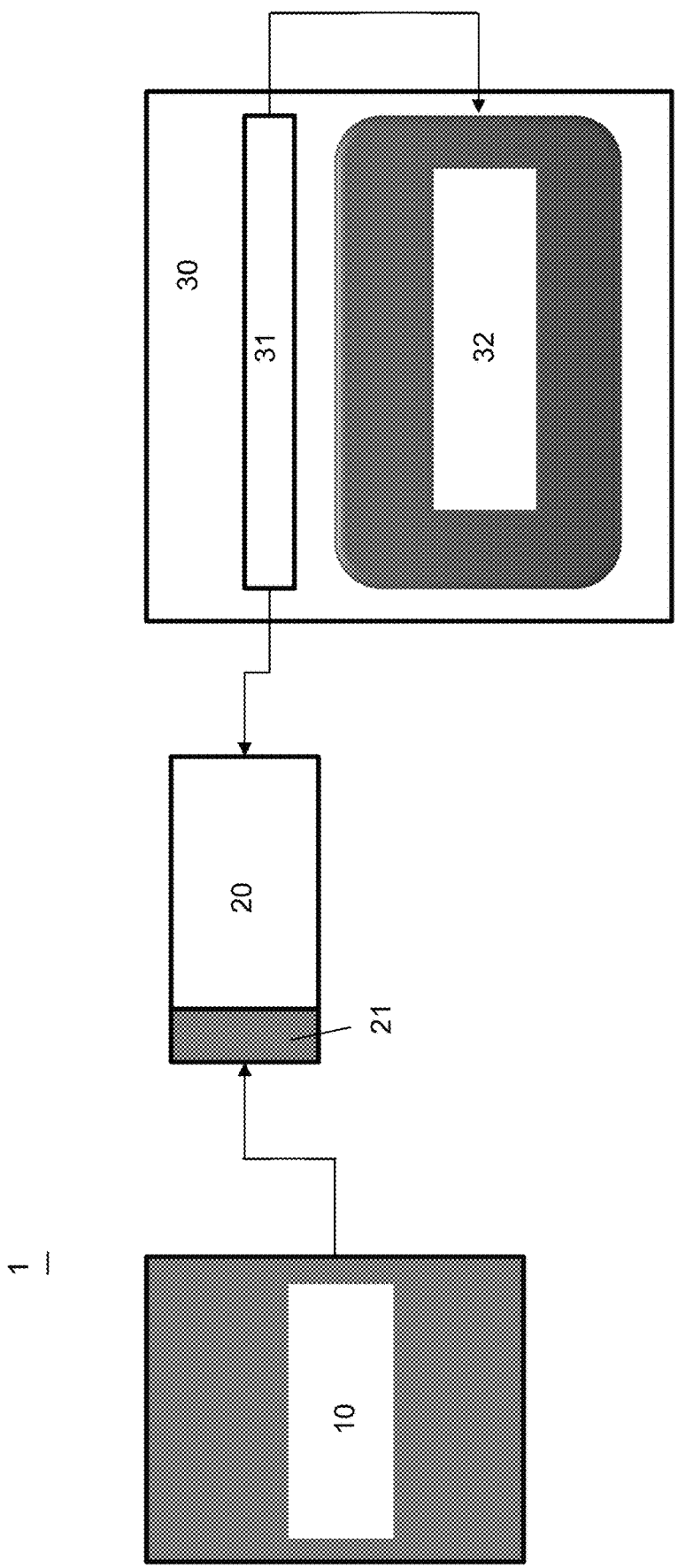
FIG. 1 shows a schematic diagram of a proxy server interface according to an exemplary embodiment.

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments.

In the accompanying figures, the size and relative sizes of layers, films, panels, regions, etc., may be exaggerated for clarity and descriptive purposes. Also, like reference numerals denote like elements. Although the terms first, second, etc. may be used herein to describe various elements, components, regions, layers, and/or sections, these elements, components, regions, layers, and/or sections should not be limited by these terms. These terms are used to distinguish one element, component, region, layer, and/or section from another element, component, region, layer, and/or section. Thus, a first element, component, region, layer, and/or section discussed below could be termed a second element, component, region, layer, and/or section without departing from the teachings of the present disclosure.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," comprising," "includes," and/or "including,"

when used in this specification, specify the presence of stated features, integers, steps, operations, elements, components, and/or groups thereof, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

Problems may arise when using biofeedback with modern technologies such as video players or "streaming" online media services. Extremely prompt (i.e., time-sensitive) responses are needed by these types of technologies during the biofeedback processes. For example, if a subject's brain waves are being measured via electroencephalogram (EEG) and are desired to be used to control playback of streaming Internet video, extremely short periods of time of less than about 200 ms are necessary to correctly interface with the video. That is, for there to be correct correspondence and correlation between the EEG measurements and the video functionality, the response time must be less than about 200 ms. If the response time is greater than about 200 ms, there may be a delay or "lag" between measured physiological or neurological functions and control of technologies like video.

Figure 2:
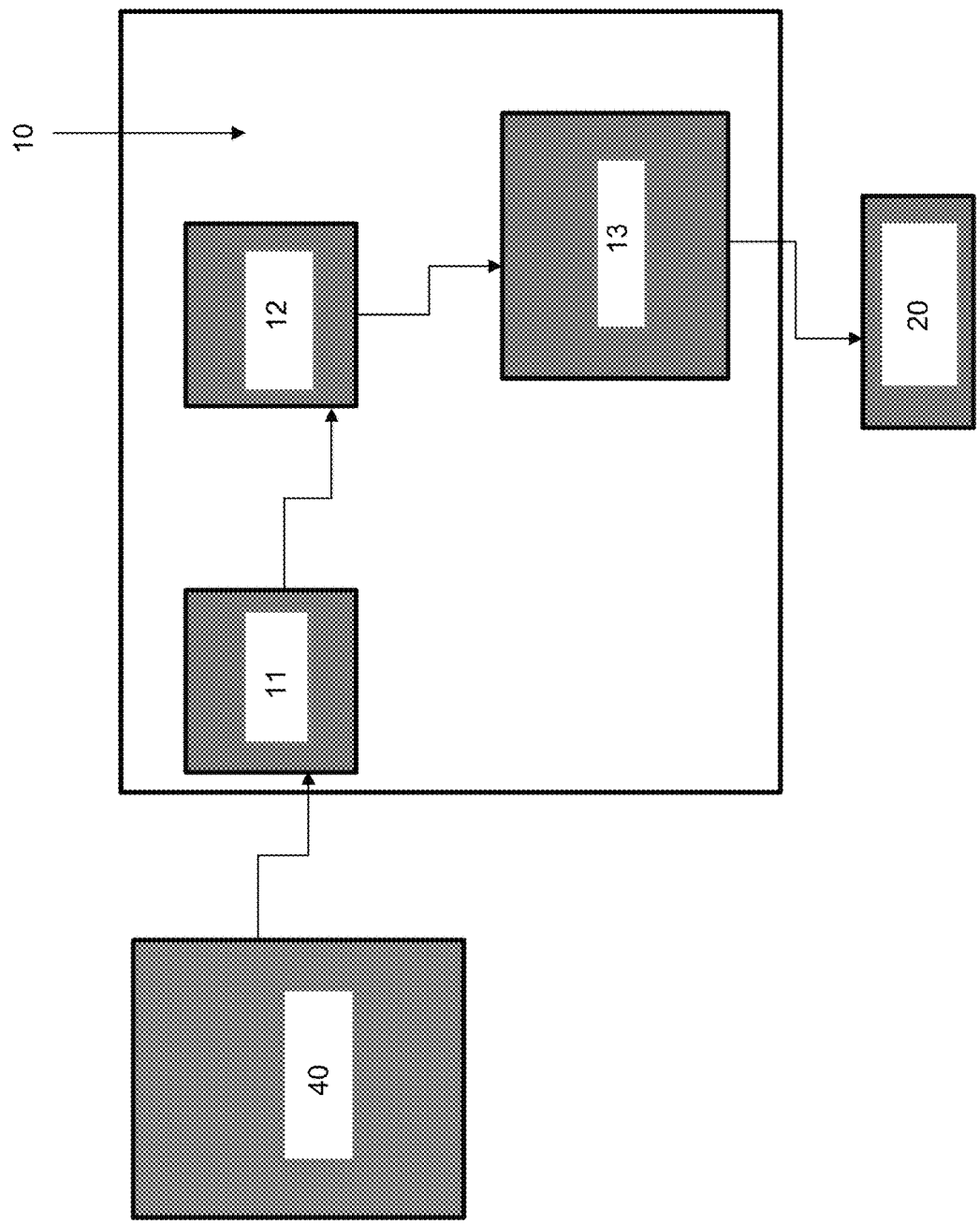
FIG. 2 shows a schematic diagram of a measurement system of the proxy server interface of FIG. 1.

As shown in FIG. 1 and FIG. 2, exemplary embodiments of the present disclosure relate to a proxy server that interfaces between measured subject functions and technologies such as streaming video. Typically, physiological or neurological functions are outputted by a measurement system as a signal to a display technology. According to the present disclosure, a call in for data from the measurement system or the display technology, for example using asynchronous communication, is stored in the proxy server. The proxy server may rely on the data output from the measurement system to control an Internet browser's functionality in order to control playback of streaming video, according to an exemplary embodiment. By buffering the data from the measurement system and the Internet browser, response time delay may be reduced below the 200 ms threshold.

A proxy server interface 1, according to an exemplary embodiment as shown in FIG. 1, movement of data from a measurement system 10 may be via a push interface, meaning the measurement system 10 sends data to the proxy server 20 on an ad hoc basis. An Internet browser 30 architecture may be a poll model for acquiring data, so it may be virtually impossible for the Internet browser 30 to directly interface with the measurement system 10. The proxy server 20 buffers the data from the measurement system 10 until the Internet browser 30 calls for it.

According to the present exemplary embodiment, there may not be a one-to-one transfer of data from the measurement system 10 to the Internet browser 30. The poll from the Internet browser 30 may occur at least every 200 ms, but the push from the measurement system 10 might be shorter or longer than 200 ms, and the push may not be on a fixed interval. For example, two or more pushes of data may come from the measurement system 10 to the proxy server 20 before a poll from the Internet browser 30 occurs. Likewise, there may be multiple polls of data by the Internet browser 30 before there is a push from the measurement system 10, and the poll may acquire the same data state as the prior poll.

The measurement system 10, according to the present exemplary embodiment, as shown in FIG. 2, a hardware sensor 11 is connected to a subject 40 such as a human, and physiological or neurological functions may be measured by the sensor 11. For example, the sensor 11 may be electrodes that measure surface electromyography (SEMG) signals generated by muscle fibers of the subject. When muscle fibers contract they produce electrically measurable action potentials. Contraction intensity may be measured via SEMG signals picked up by the electrodes, and increasing action potentials generate increased SEMG signal levels. Signals measured by the sensor 11 are outputted to an encoder 12 that converts analog signals to digital signals (i.e., data). The signals converted by the encoder 12 are then sent to a processor 13 having the special purpose of manipulating the data via at least one of processing, displaying, and recording. Once the data is manipulated by the processor 13, it may be output to the proxy server, as described above with respect to FIG. 1.

In the measurement system 10, the data may be manipulated in order to assist the subject 40 in achieving a non-invasive way to provide biofeedback, physical rehabilitation, and other clinical indications. For example, biofeedback may allow subject behavior to be modified based on a feedback loop. A graphical user interface may be included within the measurement system, which displays certain images when sensed data from the subject is determined by the processor to be within a certain desired range. In order for the subject to change their behavior, the subject may need to observe the manipulated data. That is, by observing the displayed data, the subject may know whether signals measured by the sensor should be altered or controlled by the subject itself. This data display may occur within the measurement system itself via the graphical user interface.

As shown in FIG. 2, data may be output from the measurement system 10 after manipulation by the processor 13, to the proxy server 20. The proxy server 20 may include an SDK 21 to facilitate the interface between the proxy server 20 and the measurement system 10. The data may include information relevant to the subject 40, so the subject may know whether signals measured by the sensor 11 need to be altered or controlled by the subject itself. As described above with respect to FIG. 1, data may be output by the measurement system 10 and pushed to the proxy server 20, and then polled from the proxy server by the Internet browser 30.

The Internet browser 30 may include a browser extension 31 that polls the proxy server 20 for data. The browser extension 31 may manipulate the data for use by a streaming player 32. For example, data from the measurement system 10 may be used to implement video filter controls in the streaming player 32 such as blur, contrast, brightness, and saturation. The data may also be used to implement video playback controls in the streaming player 32 such as full screen mode, play, mute, closed caption, and volume level.

As shown in the table in FIG. 3, subject biometric data from various measurement systems may be cached by the proxy server interface, such that an Internet browser extension may query the buffered data in the proxy server interface. The timing of the measured subject biometric data may vary, as shown in 100 ms intervals, which is cached by the proxy server interface. The browser extension polls at 400 ms intervals, thus the cached proxy server interface values are registered by the browser extension accordingly.

According to an exemplary embodiment, manipulated data from the measurement system that is output to the proxy server may be used to control video filter and video playback in an Internet browser, such as with a streaming video service. Since the proxy server buffers the outputted data, response times for control of video filter and video playback may be within the threshold limit of about 200 ms. The subject may observe the manipulated data in an external environment like an Internet browser without response time delay, thus permitting accurate biofeedback control.

Figure 4:
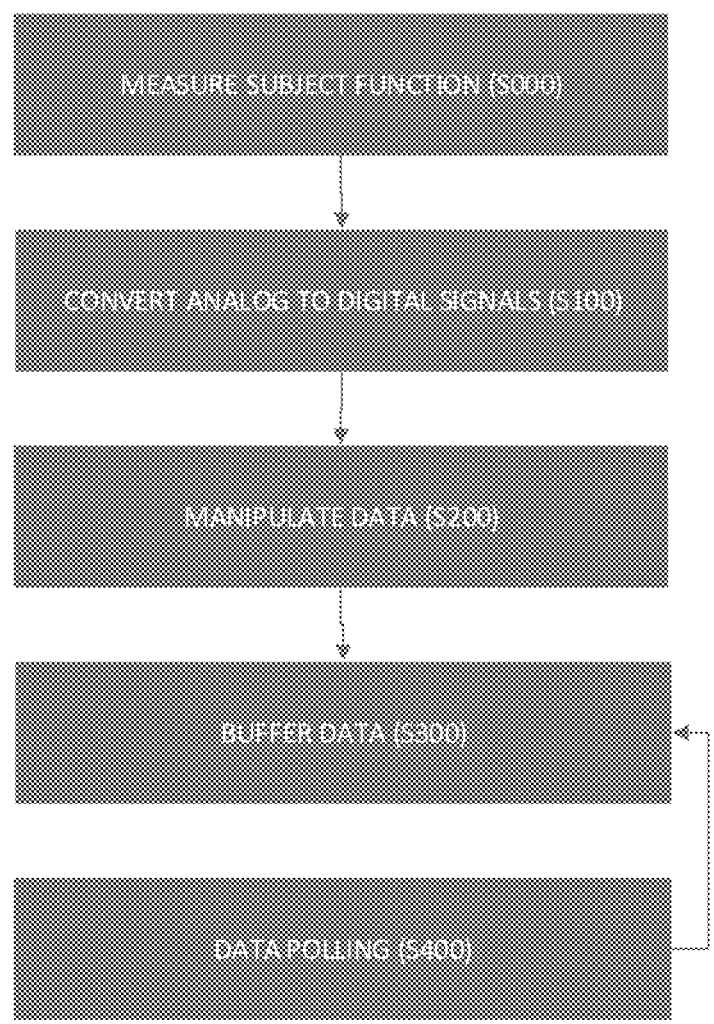
FIG. 4 is a flowchart illustrating a method of operation of the proxy server interface according to the exemplary embodiment of FIG. 1.

FIG. 4 is a flowchart illustrating a method for utilizing a proxy server interface between measured subject functions and a streaming video technology according to an exemplary embodiment. Like elements which are the same as those described above with reference to FIG. 1 and FIG. 2 are denoted by like reference numerals, and repeated descriptions will be omitted.

Referring to FIG. 4, the method for utilizing the proxy server interface is started when a hardware sensor of a measurement system measures physiological or neurological functions of a subject (S000). Then, signals measured by the sensor are outputted to an encoder that converts analog signals to digital signals (i.e., data; S100). The converted signals are then sent to a processor for manipulating the data by at least one of processing, displaying, and recording (S200). The manipulated data may be stored by a memory in the measurement system or remotely.

The data from the measurement system is then pushed to the proxy server interface, and the proxy server interface buffers the data (S300). Then, an Internet browser polls the proxy server interface (S400). Steps S000 through S300 and S400 may be repeated, for as often as the measurement system pushes data to and/or the Internet browser polls data from the proxy server interface.

Thus, step S400 (data polling) need not occur synchronously with steps S000 through S200 (data pushing). Since pushed data is buffered at step S300 by the proxy server interface, step S400 may occur asynchronously with steps S000 through S200. The buffered data may be stored by a memory in the measurement system or remotely, such as a separate computer or cloud-based non-transitory memory. The polled data by the Internet browser may be automatically retrieved and/or determined based on the buffered data in the proxy server interface.

Although certain exemplary embodiments and implementations have been described herein, other embodiments and modifications will be apparent from this description. Accordingly, the inventive concept is not limited to such embodiments, but rather to the broader scope of the presented claims and various obvious modifications and equivalent arrangements.

I claim:

1. A method for utilizing a proxy server interface, the method comprising:
measuring at least one of physiological and neurological functions of a subject by a hardware sensor in a measurement system;
generating a first signal by the hardware sensor, the first signal comprising measured information of the at least one of physiological and neurological functions;
manipulating the first signal by a processor, the measurement system comprising a first memory configured to store the manipulated signal;
outputting the manipulated signal by the measurement system to the proxy server interface;
buffering the manipulated signal by the proxy server interface in a second memory;
polling the buffered signal by an Internet browser; and
displaying an image to the subject by a graphical user interface,
wherein:
outputting the manipulated signal to the proxy server interface and polling the proxy server interface for the buffered signal occurs asynchronously; and
wherein the image is generated by a streaming player of the Internet browser.

2. The method of claim 1, wherein polling the proxy server interface for the buffered signal occurs at least once every 200 ms.

3. The method of claim 1, wherein outputting the manipulated signal to the proxy server interface further comprises pushing the manipulated signal by the measurement system on an ad hoc basis.

4. The method of claim 1, further comprising, after generating the first signal, converting the first signal from analog to digital.

5. The method of claim 4, wherein the digital signal is a data signal.

6. The method of claim 1, wherein manipulating the first signal comprises at least one of processing, displaying and recording.

7. The method of claim 1, wherein a browser extension of the Internet browser performs polling the buffered signal.

8. The method of claim 1, wherein generating the image comprises:
manipulating the buffered signal by the Internet browser; and
implementing video filter controls or video playback controls by the Internet browser.

9. The method of claim 8, wherein:
the video filter controls comprise at least one of blur, contrast, brightness, and saturation; and
the video playback controls comprise at least one of full screen mode, play, mute, closed caption, and volume level.

10. The method of claim 9, wherein the displaying the image to the subject is based on a biofeedback loop, whereby the at least one of physiological and neurological functions is altered or controlled by the subject.

11. A method for utilizing a proxy server interface, the method comprising:
measuring at least one of physiological and neurological functions of a subject by a hardware sensor in a measurement system, the hardware sensor configured to generate a first signal containing information of the at least one of physiological and neurological functions;
manipulating the first signal by a processor, the measurement system comprising a first memory configured to store the manipulated signal;
outputting the manipulated signal to the proxy server interface, the proxy server interface configured to buffer the manipulated signal in a second memory;
polling the proxy server interface for the buffered signal by an Internet browser; and
displaying an image to the subject by a graphical user interface,
wherein:
outputting the manipulated signal to the proxy server interface and polling the proxy server interface for the buffered signal occurs asynchronously; and wherein the image is generated by a streaming player of the Internet browser.

* * * * *